(12) United States Patent
Brown et al.

(10) Patent No.: US 8,668,684 B2
(45) Date of Patent: Mar. 11, 2014

(54) HOLDING DEVICE FOR MEDICAL PURPOSES

(75) Inventors: Stuart I. Brown, St. Andrews (GB); Ian Rutherford, Dundee (GB)

(73) Assignee: University of Dundee (GB)

( * ) Notice: Subject to any disclaimer, the term of this patent is extended or adjusted under 35 U.S.C. 154(b) by 1659 days.

(21) Appl. No.: 12/030,457

(22) Filed: Feb. 13, 2008

(65) Prior Publication Data

US 2008/0272251 A1 Nov. 6, 2008

(30) Foreign Application Priority Data

Feb. 13, 2007 (DE) .......................... 10 2007 006 892

(51) Int. Cl.
*A61B 1/00* (2006.01)

(52) U.S. Cl.
USPC ............................... 606/1; 901/28; 248/122.1

(58) Field of Classification Search
USPC .................... 606/1, 130; 600/102; 74/490.01, 74/490.05; 901/28
See application file for complete search history.

(56) References Cited

U.S. PATENT DOCUMENTS

| 5,824,007 A | 10/1998 | Faraz |
| 2003/0116167 A1 | 6/2003 | Hooser |

FOREIGN PATENT DOCUMENTS

| DE | 3026160 A1 | 2/1982 |
| DE | 4316590 A1 | 11/1993 |
| DE | 19526915 B4 | 2/1997 |
| DE | 10319457 A1 | 11/2003 |
| EP | 0730320 A2 | 9/1996 |
| WO | 0043685 A1 | 7/2000 |
| WO | 2004053382 A1 | 6/2004 |

OTHER PUBLICATIONS

European Search Report; Application No. EP 08 00 2229; Issued: Mar. 14, 2011; 6 pages.
German Search Report, Sep. 18, 2007, 4 pages.

*Primary Examiner* — Bill Thomson
*Assistant Examiner* — Jeffrey Lipitz
(74) *Attorney, Agent, or Firm* — St. Onge Steward Johnston & Reens LLC

(57) ABSTRACT

A holding device for medical purposes having a carrier arm on whose distal end a medical instrument can be secured and having at least one joint for positioning the carrier arm and/or the medical instrument, where the joint can be converted between the position that releases the joint and the position that blocks the joint. The holding device provides simple operation, reliable positionability, and can be cleaned well. The joint comprises at least two joint members that enter into active connection with one another by mutually engaging catching elements, where the catching elements are positioned essentially perpendicular to the longitudinal direction of the carrier arm and are pre-tensed with respect to one another by a spring element, and that in the joint at least one hydraulically or pneumatically spreadable expansion element is positioned by which the joint can be converted into the position that releases the joint.

20 Claims, 4 Drawing Sheets

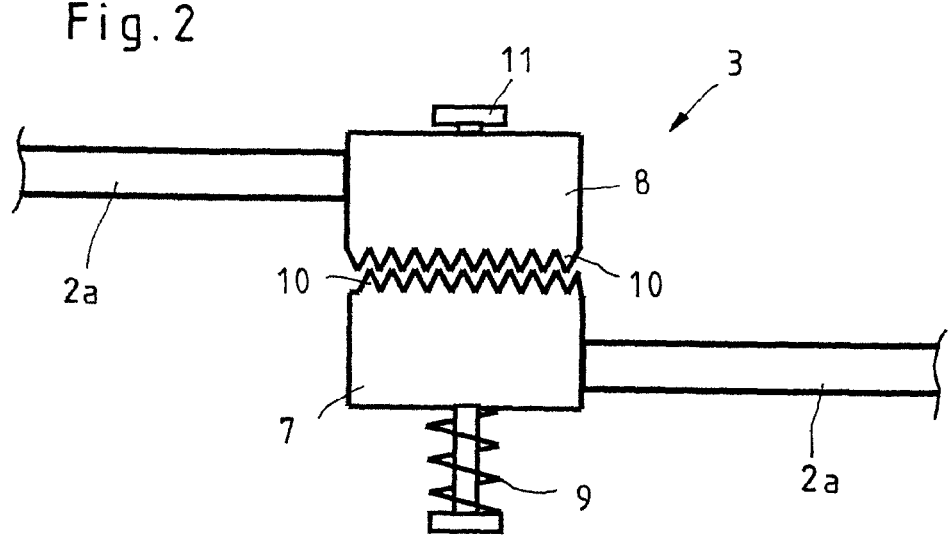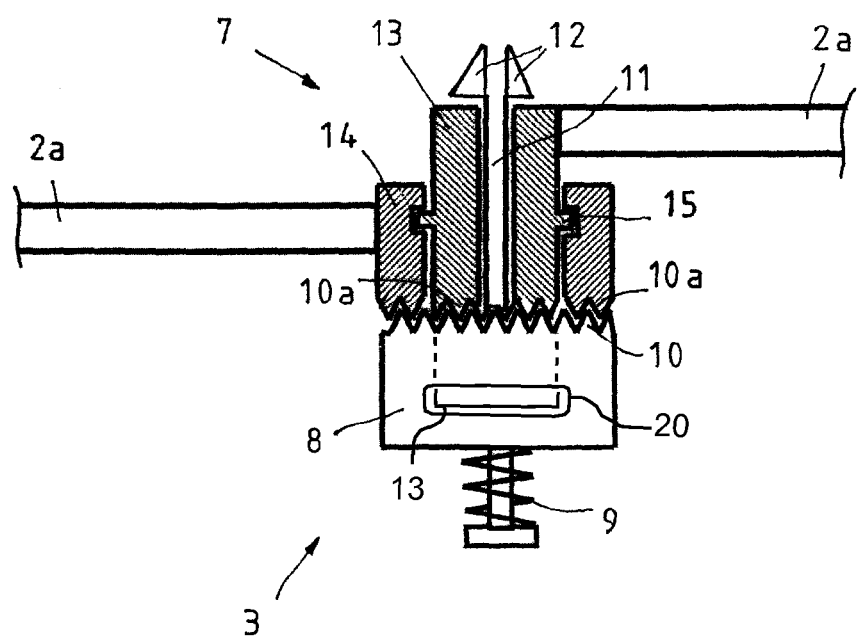

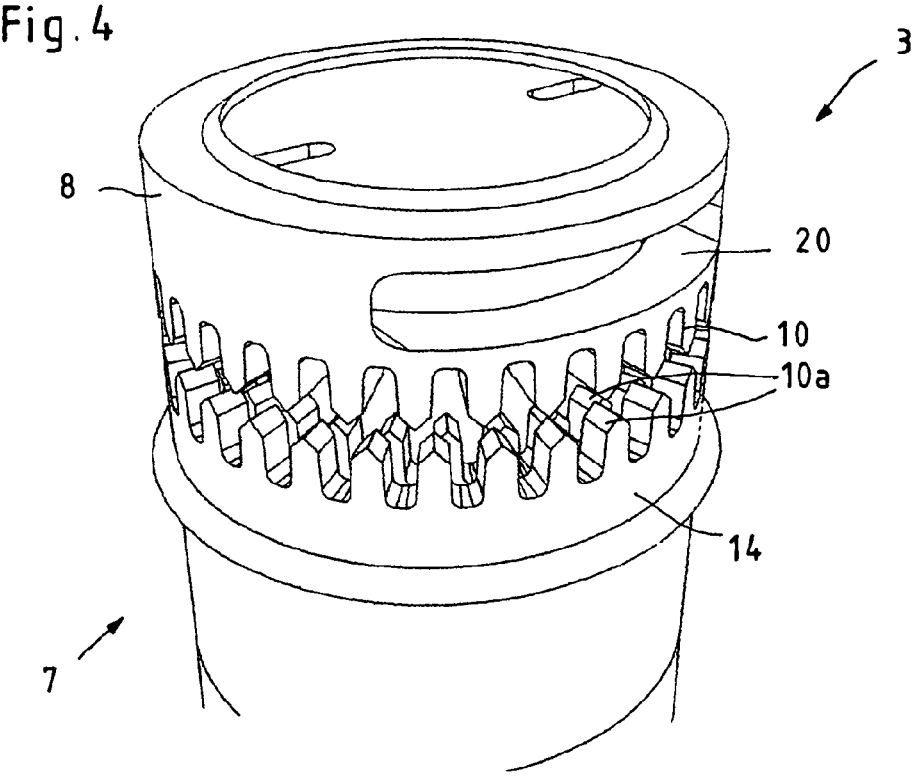
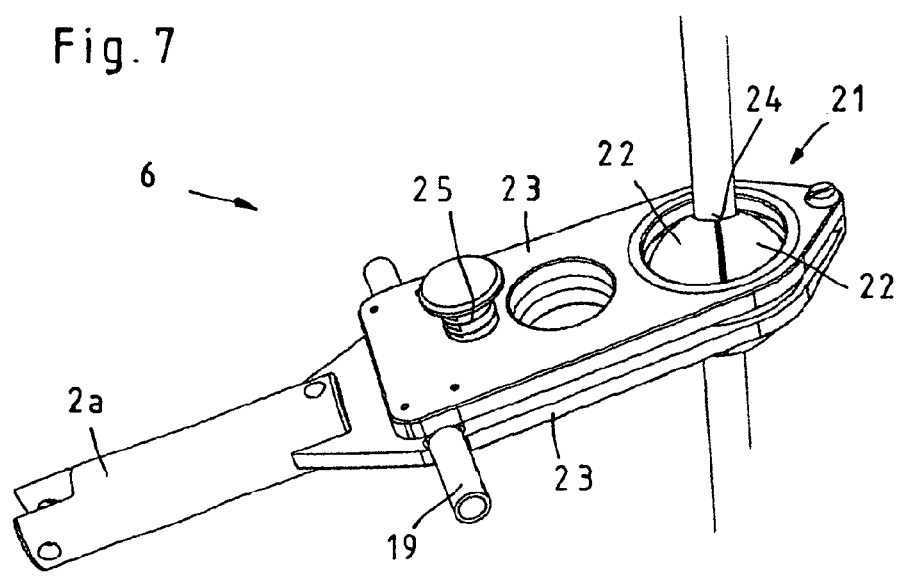

HOLDING DEVICE FOR MEDICAL PURPOSES

CROSS-REFERENCE TO RELATED APPLICATIONS

The present application claims priority of German patent application No. 10 2007 006 892.3 filed on Feb. 13, 2007, the content of which is incorporated herein by reference.

FIELD OF THE INVENTION

The invention relates to a holding device for medical purposes having a carrier arm on whose distal end at least one medical instrument can be secured in an instrument intake, and having at least one joint for positioning the carrier arm and/or the medical instrument, wherein the at least one joint can be displaced between the position that releases the joint and the position that stops the joint.

BACKGROUND OF THE INVENTION

Holding devices of this type are frequently required in performing surgical interventions in order to hold medical instruments of various types, such as retractors, video cameras, or endoscopes, in an established position for a fairly long period. Owing to the jointed design of the holding devices, it is possible for the surgeon to position with exactitude the medical instrument that is held in the instrument intake and, by stopping the joint or joints, to fix the position of the holding device that has been selected.

A generic holding device is known in the art, for instance, from patent US 2003/116167 A1. In this known holding device the joints consist of two joint members, which enter into active connection with one another by means of catching elements that engage with one another, where each joint comprises an inflatable balloon, which when it is expanded presses the catching elements into engagement with one another. The disadvantage with this known construction is that the carrier arm members immediately rotate toward one another when there is any drop in pressure in the bladder, because the reciprocal engagement of the catching elements of the joint members is produced exclusively by the applied pressure of the bladder.

An additional holding device is known for instance from patent DE 195 26 915 B4. With this known holding device, the joint members are locked in place with respect to one another by friction through the spring force of at least one spring element. This blocking is released pneumatically by vanes that are positioned in the joint and when acted upon by compressed air, for instance, ensure a release of the friction locking. Although holding devices of this type have been thoroughly proven in the art, the contact surfaces that are held together by the friction locking in fact cause problems with cleansing, because owing to the high contact forces required to produce a reliable friction lock, scratches can be produced on contact surfaces that in turn can form germ cells leading to soiling.

In addition, a holding device is known from patent DE 43 16 590 A1. With this known holding device, the joint mechanism takes the form of a toothed wheel work, where the engagement of the toothed gears configured as inner and outer wheel sprockets is directed parallel to the longitudinal direction of the carrier arm, that is, parallel to the axis of rotation, and the wheel sprockets are held engaged with one another by means of a pressure force acting axially. A disadvantage of this construction is that it requires extreme precision in manufacturing the wheel sprockets in order to ensure interlocking engagement of the teeth of both wheeled sprockets without free play. The axial spring force prevents only the separation of the two wheel sprockets, as it is not possible with this configuration to prevent free play in the horizontal direction.

It is consequently the object of the invention to create a holding device for medical purposes that combines ease of operation and reliable positionability with effective cleansing.

SUMMARY OF THE INVENTION

This object is fulfilled by the invention in that the at least one joint consists of at least two joint members, which come into active connection with one another by means of mutually intersecting catching elements, where the reciprocal catching elements are positioned essentially perpendicular to the longitudinal direction of the carrier arm and are pre-tensed with respect to one another by means of at least one spring element and in that at least one hydraulically or pneumatically spreadable expansion element is positioned in the joint so that by said element the at least one joint can be moved hydraulically or pneumatically into the position that releases the joint.

Owing to the inventive configuration of the joint mechanism as catching elements that are positioned essentially perpendicular to the longitudinal direction of the carrier arm and engaging with one another, it is possible to produce a joint mechanism that, on the one hand, is easy to operate and, on the other hand, ensures a positioning of the carrier arm that is essentially without free play. Because the catching elements engage with one another perpendicularly to the longitudinal direction of the carrier arm and the joint members are axially pre-tensed, the engagement of the catching elements with one another is strengthened without leaving any free play for relative movement of the joint members with respect to one another.

Moving the joint into the position that releases the joint and is thus adjustable occurs, according to the invention, hydraulically or pneumatically, and for this purpose at least one hydraulically or pneumatically spreadable expansion element is positioned in the joint. Because of the axial pre-tensing of the joint members and the use of the spreadable expansion element exclusively to release the joint connection, the inventive holding device remains in the exactly positioned posture even with a decline in pressure.

According to a preferred embodiment of the invention it is proposed that the expansion element should be configured as a hose. The configuration of the expansion element as a hose fed through the joint constitutes a particularly simple and cost-effective way of achieving the pneumatic or hydraulic separation of the joint members. For positioning the hose in the joint, a passageway for the hose is opened up in at least one of the joint members that can be placed in active connection with one another.

For mounting the hose in the joint, a passageway for the hose is opened up in at least one of the joint members that can be brought into active connection with one another.

To achieve the most precise possible positioning of the medical instrument that is to be aligned, the carrier arm is advantageously configured according to the invention to be in several parts, so that the individual carrier members are connected rotatably with one another by the joints.

For configuring the catching elements, it is proposed with a preferred embodiment of the invention that the catching elements should be configured as toothed wheels mounted on the front surfaces of the joint members that are facing one another. The configuration of the catching elements in the manner of a Hirth coupling is a simple way to make possible an exact clearly measured adjustment of the desired holding position of the carrier arm. Thanks to the use of two or more joints on a holding device, any desired adjustment angle can be selected as well in the use of toothed wheels as joint mechanism. With each additional joint, the free play for movement of the carrier arm is increased by one degree of freedom.

It is proposed with a preferred embodiment of the invention that at least one joint member should be configured in several parts in such a way that these partial elements comprise coaxial wheel sprocket rings, where the wheel sprocket rings of the partial elements can advantageously be rotated with respect to one another but independently of one another in the position that releases the joint and can be blocked so that they cannot rotate with respect to one another in the position that blocks the joint.

The coupling of the coaxial wheel sprockets among themselves is achieved according to the invention by means of a groove-and-spring connection, which ensures reciprocal guidance of the wheel sprockets.

According to a practical embodiment of the invention, it is proposed that one joint member should be constructed in two parts and should consist of an inner cylindrical core and an outer ring that surrounds the core coaxially.

To ensure that the reciprocal engagement of the toothed gears is guaranteed at all times, even with weight forces of various sizes on the ends of the components that are to be connected to one another by the joint and on the various leverage forces connected with them, it is proposed with the invention that both components that are to be connected with one another by means of the joint, in particular the carrier arm members, should be secured on the two-part joint member in such a way that one component/carrier arm is connected with the inner cylindrical core and the other component/carrier arm member is connected with the outer ring. By positioning both components/carrier arm members on the same side of the toothed ring, it is possible to avoid having the various forces that arise press the gear tooth apart.

The reciprocal securing of the wheel sprockets of the multi-partite joint member in the stopped position of the joint is advantageously brought about according to the invention in such a way that the gear tooth of the other joint member that is in active connection with the multi-partite joint member is configured as broad enough so that it is engaged, in the position that blocks the joint, with all the sprocket wheel rings of the multi-partite joint member.

With an alternative embodiment of the invention it is proposed that the catching elements should be configured as pins and catching recesses for form-locking insertion of the pins, so that the catching recesses advantageously should be configured as holed ring disks on one of the joint members that can be interlocked with the corresponding pins of the other joint members.

To produce the reciprocal pre-tensing between the two joint members by means of the at least one spring element, it is proposed according to a preferred embodiment of the invention that the at least one spring element is supported on one joint member to produce the pre-tensing between the joint members and the spring force is transmitted to the other joint member by a tensing element connected with the spring element, so that the tensing element advantageously comprises catching hooks for securing to the joint member that is to be pressed on.

The pre-tensing between the two joint members that are in active connection can according to the invention be adjusted by the at least one spring element, where this adjustment can be carried out through the selection of a spring element with the desired spring direction line or through pre-tensing of the spring element, for instance by means of a tensing screw or the like.

It is further proposed with the invention that the instrument intake should be configured as a ball bearing, where the bearing ball consists of two hemispheres and the bearing shell consists of two plates that can be pre-tensed with respect to one another and where the diameter of the recesses is slightly smaller than the diameter of the bearing balls.

The actual holding of the medical instrument in the instrument intake is carried out according to the invention by means of a passage opening configured in the area of the contact surfaces of the two hemispheres that make up the bearing ball for clamped intake of the medical instrument that is to be held.

The clamped mounting of the medical instrument between the two hemispheres of the ball bearing can be released according to the invention hydraulically or pneumatically, for which purpose at least one hydraulically or pneumatically spreadable expansion element is positioned advantageously in the ball bearing.

It is finally proposed with a practical embodiment of the invention that the expansion element should be configured as a hose.

Additional characteristics and advantages of the invention can be seen from the appended illustrations showing various embodiments of an inventive holding device for medical purposes in simple exemplary manner, without restricting the scope of the invention to these embodiments.

BRIEF DESCRIPTION OF THE DRAWINGS

FIG. 2 shows a schematic side view of a first embodiment of a joint for an inventive holding device for medical purposes.

FIG. 3 shows a schematic side view of a second embodiment of a joint for a holding device.

FIG. 4 shows a perspective view of the joint seen in FIG. 3.

FIG. 7 shows a schematic perspective view of an instrument intake for an inventive holding device for medical purposes.

DETAILED DESCRIPTION OF THE INVENTION

Figure 1:
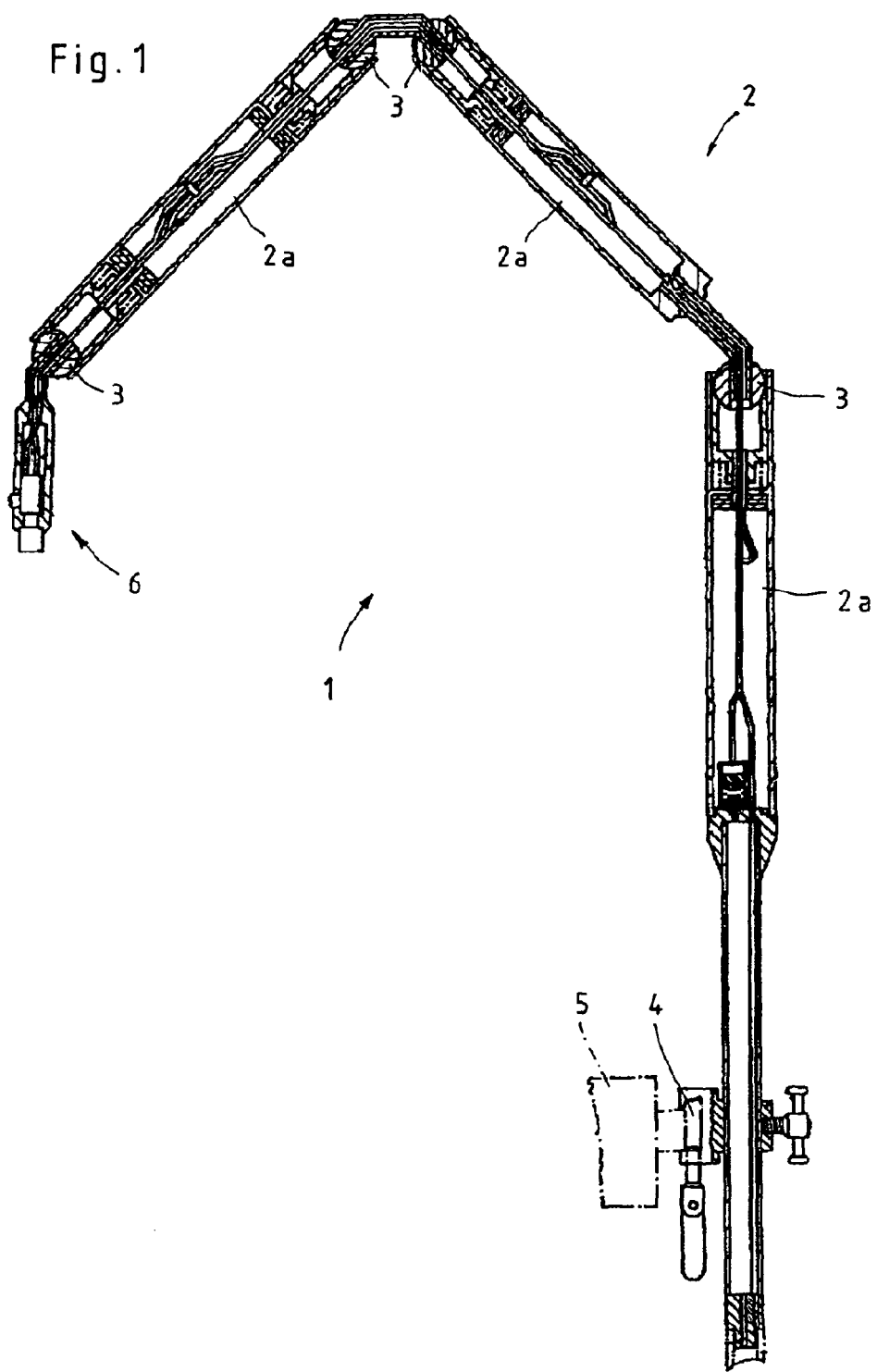
FIG. 1 shows a holding device for medical purposes according to the state of the art.

The first illustration (FIG. 1) shows a holding device for medical purposes according to the state of the art. This holding device 1 consists essentially of a carrier arm 2 bearing several carrier arm members 2a, where the individual carrier arm members 2a of the carrier arm are connected to one another by joints 3 that can rotate with respect to one another.

Holding devices 1 of this type are often required in carrying out surgical procedures in order to hold medical instruments of many types such as retractors, video cameras, or endoscopes in a particular position for an extended period. As a result of the jointed configuration of the holding device 1 it is possible for the surgeon to position the medical instrument precisely and to secure the assumed position of the holding device 1 by blocking the joint 3 or the joints 3. In addition to endoscopic surgery, such holding devices 1 are also applied in open surgery.

In the area of its proximal end, the carrier arm 2 can be affixed by means of a chucking device 4, for instance to the operating table 5. On the distal end the carrier arm 2 comprises an instrument intake 6 for installing the medical instrument that is to be positioned by means of the holding device.

As an alternative to the structure of the carrier arm 2 illustrated in FIG. 1, made up of several carrier arm members coupled one after the other and connected to one another by joints 3, it is also possible of course to configure the carrier arm 2 with multiple arms in such a way that, starting from one joint 3, several carrier arm members 2a point in various directions. These carrier arm members 2a, for their part, can be coupled in turn by joints 3 with additional carrier arm members and can each be configured on their distal ends with instrument intakes 6 for inserting the medical instruments that are to be positioned by the holding device 1.

The structure of the joints 3 can be seen from FIGS. 2 through 6 and from the instrument intake 6 seen in FIG. 7.

As can be seen in FIGS. 2 through 6, the joints 3 consist of two joint members 7 and 8, which enter into active connection with one another by means of mutually engaging catching elements, so that the reciprocal catching elements are directed essentially perpendicularly to the longitudinal direction of the carrier arm 2 and are pre-tensed with respect to one another by means of at least one spring element 9.

In the two embodiments illustrated in FIGS. 2 through 4, these catching elements are configured as toothed wheels 10 configured on the front surfaces of the joint members 7 and 8 facing one another in the manner of a Hirth coupling. The teeth of the toothed wheels 10 here are advantageously configured as conically tapering in order to achieve an automatic gliding of the toothed elements 10 into one another with as little free play as possible, as soon as the joint members 7 and 8 are pressed against one another by means of the spring element 9. The direct reciprocal engagement of the toothed wheels 10 free of a dead spot is further facilitated in that the points of the teeth are configured as rounded off or sloping, so that when two teeth of the toothed wheels 10 meet, the teeth are always diverted to the side into the position that produces the interconnecting of the toothed elements.

As can further be seen from FIGS. 2 through 4, the spring element 9 that causes the pre-tensing between the joint members 7 and 8 of the joint 3 is supported on the joint member 7 or 8 and transmits the spring force to the other joint member 8 or 7 by means of a tensing element 11 that is connected with the spring element 9.

In the embodiment shown in FIG. 3, the tensing element 11 in addition comprises, on its free end extending beyond the joint member 7, radially spring-elastic catching hooks 12 for securing to the joint member 7 that is to be pressed onto it. Because of the spring elasticity in the radial direction, the catching hooks 12 act like a snapping lock, so that the joint member 7 that is mounted on the free end of the tensing element 11 is held securely positioned in the correct alignment to the other joint member 8 without further assembly activity. To disassemble the joint member 7, it is necessary in this embodiment only to press the catching hooks 12 radially inward in order thereafter to be able to withdraw the joint member 7 from the tensing element 11.

To ensure that the reciprocal engagement of the toothing elements 10 is constantly ensured even with forces of varying weight applied to the ends of the components that are to be connected with one another by the joint 3, for instance carrier arm members 2a of the carrier arm 2, and the varying leverage forces connected with them, in the embodiments illustrated in FIGS. 3 and 4 both components/carrier arm members 2a connected with one another by the joint 3 are secured on the same joint member 7. For this purpose the joint member 7, as can be seen in particular from FIG. 3, is made up of an inner cylindrical core 13 and an outer ring 14 that coaxially surrounds the core 13.

Positioning both components/carrier arm members 2a on the same side of the toothed wheel 10 prevents the arising different forces of the toothed wheel 10 from being pressed apart from one another.

The bi-partite joint member 7 is configured in such a way that the individual components, that is the core 13 and the ring 14, comprise coaxial wheel sprocket rings 10a, and the wheel sprocket rings 10a of the components 13, 14 can be rotated relative to one another independently of one another in the position that releases the joint 3 and are blocked firmly against rotation with respect to one another in the position that blocks the joint 3. Because of the multi-partite configuration of one joint member 7 with the rotatable wheel sprockets 10a, the adjustment range of the components that are to be connected with one another by the respective joint 2 is clearly increased.

The coupling of the two components 13, 14 of the joint member 7 with one another and thus also of the coaxial wheel sprockets 10a is carried out by a groove-and-spring connection 15, which ensures a reciprocal control of the components 13, 14 or of the wheel sprockets 10a.

Figure 5:
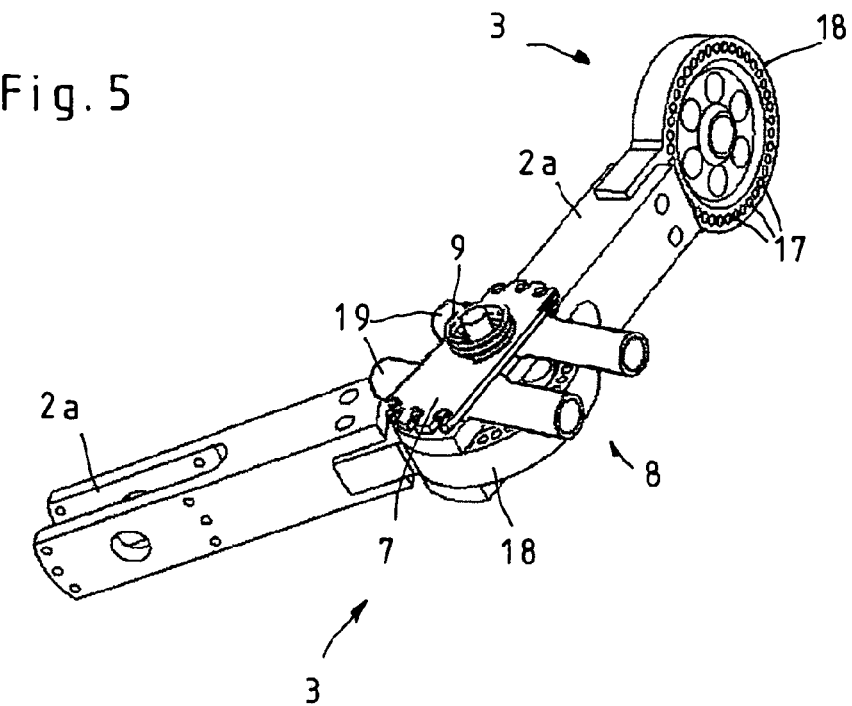
FIG. 5 shows a schematic perspective side view of a third embodiment of a joint for an inventive holding device, showing the joint in the blocked position
Figure 6:
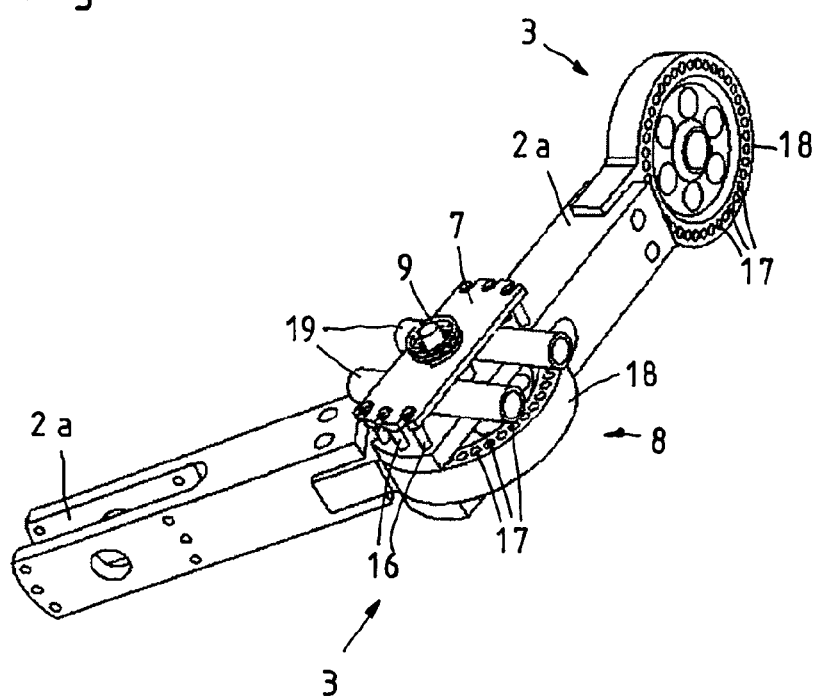
FIG. 6 shows a view according to FIG. 5 but showing the joint in the released position.

In the alternative embodiment illustrated in FIGS. 5 and 6, the catching elements that come into active connection with one another and are aligned essentially perpendicular to the longitudinal direction of the carrier arm 2 are configured as pins 16 and catching recesses 17 for form-locking intake of the pins 16, where the catching recesses 17 are configured as a holed ring disk 18 on the joint member 8, which can be brought into engagement with the pins 16 mounted on the other joint member 7.

For all previously described embodiments for configuring the catching elements that are positioned essentially perpendicular to the longitudinal direction of the carrier arm 2, namely the toothed interlockings 10 and the combination of pins 16 and catching recesses 17, FIGS. 5 and 6 depict in exemplary manner the way the joint 3 can be converted from the position that blocks the joint 3, and in which the toothed engagements 10 intersect or in which the pins 16 engage in the catching recesses 17, into a position that releases the joint 3, and in which the joint 3 makes possible the precisely positioned adjustment relative to one another of the components/carrier arm members 2a that are connected to one another by the joint 3.

Transferring the join 3 into the position that releases the joint 3 occurs hydraulically or pneumatically by means of an expansion element 19 that is positioned in the joint 3 and is configured as a hose 19 in the illustrated embodiment. Alternative embodiments such as in the form of inflatable airbag or the like are also possible.

Configuring the expansion element 19 as a hose 19 constitutes a particularly simple and cost-effective variant. The use of the expansion elements 19 configured as hoses 19 is advantage for hygienic reasons as well, because the hoses 19 on the one hand can be completely sterilized and on the other hand and also can be used as throwaway articles that are not to be cleaned because of their low price.

In the embodiment illustrated in FIGS. 5 and 6, two hoses 19 are used, but depending on the design structure of the joint 3 that is to be separated, the use of just one hose 19 is also sufficient, as can be seen for example from FIG. 4, in which a passageway 20 for a hose 19 is opened up in the joint member 8.

In the blocked position of the joint 3 shown in FIG. 5, the hoses 19 positioned in the joint 3 between the joint members 7 and 8 interconnected by the spring element 9 are pressed together until the joint member 7 and 8 interlock in form-locking connection.

To release the form-locking connection, the hoses 19 are impacted with a fluid, for instance compressed air, so that the hoses 19 expand and assume the form shown in FIG. 6. The expansion of the hoses 19 causes the joint member 7 and 8 to be pressed out of engagement with one another, so that the joint 3 then can be transferred into a new angle position to guide the carrier arm 2 as well as the medical instrument that is to be positioned.

The possibility of hydraulic or pneumatic dissolution of the joint connection has enormous advantages in practice, because the release of the joint 3 or of joints 3 can be carried out without assistance of a tool or other direct manual activity on the joint 3. The operator merely needs to release the fluid conduit to the hoses 19 by means of a hand or foot switch in order then to be able to reposition the particular joint 3. In this way it is of course possible to connect the individual joints 3 of a holding device 1 with the fluid conduit in such a way that each joint 3 can be powered individually, individual joints 3 are brought together as joint groups, or all joints 3 are impacted simultaneously with the fluid in order to convert the joint 3 into the releasing position.

In addition, the pressure force required by the fluid to dissolve the form-locking connection of the joint members 7 and 8 can be adjusted by the pre-tensing exerted by the spring element 9 on the joint member 7 and 8 through the selection of corresponding pressure springs and/or pre-tensing of the spring element 9, for instance, by a tensing screw. Thus, with the sequential switching of several joints 3 onto one fluid line, it is also possible to configure the release of the joints 3 selectively if varying fluid pressures are necessary because of the varying pre-tensing of the joints 3 by the spring elements 9 in order to move the joint members 7 out of engagement with one another.

FIG. 7 finally shows a possible embodiment for configuring the instrument intake 6.

In the illustrated embodiment, the instrument intake 6 is configured as a ball bearing 21, where the bearing ball consists of two hemispheres 22 and the bearing shell consists of two plates 23 that can be pre-tenses against one another and are equipped with recesses for the balls and where the diameter of the recesses is slightly smaller than the diameter of the bearing ball.

For clamping intake o the medical instrument that is to be held, in the area of the contact surfaces of the two hemispheres 22 that make up the bearing ball, a passage bore-hole 24 is opened up, in which the medical instrument is inserted. As soon as the two plates 23 are pressed together by the spring element 25, the hemispheres 22 that are housed in the recesses of the plates 23 are pressed together in such a way that the medical instrument mounted in the passage bore-hole 24 is held by clamping in the ball bearing 21.

To facilitate the installation and reciprocal positioning of the two hemispheres 22 with respect to one another, guide elements of the groove-and-spring connection type can be formed for instance in the longitudinal direction of the passage bore-hole 24.

The clamping holder in the ball bearing 21 is released hydraulically or pneumatically here as well, by means of an expansion element 19 positioned in the ball bearing 21, for instance the hose 19 shown in FIG. 7.

A holding device 1 for medical purposes of the type described here is characterized in that the joints 3 serving for the exact positioning of the medical instrument mounted in the instrument intake 6 are simple to handle and to clean. It is particularly decisive in the handling that the joints 3 can be released hydraulically or pneumatically, so that the operator can affect the release of the joints 3 also with just a single handle or even without using his hands.

What is claimed is:

1. A holding device for medical purposes having a carrier arm on whose distal end at least one medical instrument can be secured in an instrument intake and having at least one joint for positioning one or more of the carrier arm and the medical instrument, where the at least one joint can be converted between a position that releases the joint and a position that blocks the joint, wherein the at least one joint consists of at least two joint members, which enter into active connection with one another by means of catching elements that engage with one another, where the catching elements are aligned essentially perpendicular to the longitudinal direction of the carrier arm and are pre-tensed with respect to one another by at least one spring element, and that in the joint at least one hydraulically or pneumatically spreadable expansion element is positioned by which the at least one joint can be hydraulically or pneumatically converted into the position that releases the joint; wherein the at least one spring element is supported on a joint member to produce the pre-tensing between the joint members and transmits the spring force to the other joint member by means of a tensing element connected with the spring element.

2. The holding device according to claim 1, wherein the expansion element is configured as a hose.

3. The holding device according to claim 2, wherein in at least one of the joint members that can be brought into active connection with one another, a passage bore-hole is made for the hose.

4. The holding device according to claim 1, wherein the carrier arm is configured as several individual carrier arm members, and the individual carrier arm members are rotatably connected to one another by one or more joints.

5. The holding device according to claim 4, wherein the catching elements are configured as toothed devices configured on the front surfaces of the joint members that face one another.

6. The holding device according to claim 5, wherein at least one joint member is configured in several components in such a way that these components comprise coaxial wheel sprocket rings.

7. The holding device according to claim 6, wherein the wheel sprocket rings of the components in the position that releases the joint can be rotated relative to one another independently of one another and are blocked firmly against rotation with respect to one another in the position that blocks the joint.

8. The holding device according to claim 6, wherein the components of the at least one joint member are connected to one another by groove-and-spring connections.

9. The holding device according to claim 6, wherein one joint member is of bi-partite configuration having two components and consists of an inner cylindrical core and an outer ring that coaxially surrounds the core.

10. The holding device according to claim 9, wherein at least two carrier arm members that are connected with one another by the joint are secured on the bi-partite joint member in such a way that one carrier arm member is connected with the inner cylindrical core and the other carrier arm member is connected with the outer ring.

11. The holding device according to claim 6, wherein the toothed devices of the other joint member that is in active connection with the at least one joint member configured in several components are configured so broadly that said toothed devices are engaged with all the wheel sprocket rings of the at least one joint member configured in several components in the position that blocks the joint.

12. The holding device according to claim 1, wherein the catching elements are configured as pins and catching recesses for form-locking insertion of the pins.

13. The holding device according to claim 12, wherein the notching recesses are configured as a holed disk on one of the joint members that can be brought into engagement with the corresponding pins of the other joint member.

14. The holding device according to claim 1, wherein the tensing element comprises notching hooks for securing the tensing element to the joint member to which the spring force is to be transmitted.

15. The holding device according to claim 1, wherein the pre-tensing force of the joint can be adjusted by the at least one spring element.

16. The holding device according to claim 1, wherein the instrument intake is configured as a ball bearing, where the bearing ball consists of two hemispheres and the bearing case consists of two plates that can be tensed with respect to one another and is equipped with recesses for the bearing ball and where the diameter of the recesses is slightly smaller than the diameter of the bearing ball.

17. The holding device according to claim 16, wherein in the area of the contact surfaces of the two hemispheres that form the bearing ball, a passage bore-hole is configured for clamping insertion of the medical instrument that is to be held.

18. The holding device according to claim 16, wherein the plates that form the bearing case can be converted hydraulically or pneumatically into a position that releases the bearing ball.

19. The holding device according to claim 18, wherein at least at one hydraulically or pneumatically spreadable expansion element is positioned in the ball bearing.

20. The holding device according to claim 19, wherein the expansion element is configured as a hose.

\* \* \* \* \*